United States Patent [19]

Joseph

[11] Patent Number: 4,902,292
[45] Date of Patent: Feb. 20, 1990

[54] VITREOUS BODY PROSTHESIS DEVICE

[76] Inventor: Neil H. Joseph, P.O. Box 8241, Dhahran 31311, Saudi Arabia, Saudi Arabia

[21] Appl. No.: 167,352

[22] Filed: Mar. 14, 1988

[30] Foreign Application Priority Data

Mar. 30, 1987 [GB] United Kingdom ................. 8707503

[51] Int. Cl.$^4$ ........................... H61F 2/14; H61F 2/16
[52] U.S. Cl. ........................................... 623/4; 604/9; 604/294; 623/6
[58] Field of Search ............................... 623/4, 6, 11; 128/897–899; 604/8, 9, 294

[56] References Cited

U.S. PATENT DOCUMENTS

| 4,253,199 | 3/1981 | Banko | 623/6 |
| 4,373,218 | 2/1983 | Schachar | 623/6 |
| 4,585,457 | 4/1986 | Kalb | 623/6 |
| 4,604,087 | 8/1986 | Joseph | 604/294 X |
| 4,685,447 | 8/1987 | Iversen et al. | 623/11 X |

FOREIGN PATENT DOCUMENTS 2124500A 2/1984 United Kingdom ..................... 623/6

OTHER PUBLICATIONS

Chan, C. and Okun, E., "The Question of Ocular Tolerance to Intryitreal Liquid Silicone, a Long-Term Analysis": Ophthalmology, 93:651–660, 1986.
Leaver, P. K., "Complications of Silicone Oil", Basic and Advanced Vitreous Surgery, pp. 387–388, 1986.
Charles, S., "Vitreous Substitutes", page 230 in Retinopathy of Prematurity, Current Concepts and Controversies, edited by McPherson, A. R., Kittner, H. M., Kretzer, F. L., Decker, B. C. Inc., Philadelphia 1986.
Yeo, J. H., Glaser, B. M., Michels, R. G., "Silicone Oil in the Treatment of Complicated Retinal Detachments", Ophthalmology, 94:1109–1113, 1987.
Gonvers, M., "Temporary Silicone Oil Tamponade in the Management of Retinal Detachment with Proliferative Vitreoretinopathy", American Journal of Ophthalmology, 100:239–245, 1985.
Schafer, D. M., "The Evolution of Vitreous Surgery in the U.S.", New and Controversial Aspects of Vitreoretinal Surgery, edited by McPherson, A. R., C. V. Mosby Co., St. Louis, pp. 6–8, 1977.
Aaberg, T. M., Abrams, G. W., & Edelhauser, H. F., "Intraocular Sulfur Hexafluoride, An Experimental and Clinical Correlation: New and Controversial Aspects of Vitreoretinal Surgery", edited by McPherson, A. R., C. V. Mosby Co., St. Louis, pp. 393–396, 1977.
Constable, I. J., "The Rational Selection of Vitreous Substitutes: New and Controversial Aspects of Vitreoretinal Surgery", edited by McPherson, A. R., C. V. Mosby Co., St. Louis, pp. 387–392, 1977.
Leaver, P. K., Grey, R. H. B., and Garner, A., "Silicone Oil Injection in the Treatment of Massive Preretinal Retraction. II Late Complications in 93 Eyes", British Journal of Ophthalmology, 63:361–367, 1979.
Crisp, A., DeJuan, E., and Tiedeman, J., "Effect of Silicone Oil Viscosity on Emulsification", Archives of Ophthalmology, 105:546–550, 1987.

(List continued on next page.)

Primary Examiner—Ronald L. Frinks
Attorney, Agent, or Firm—Wolf, Greenfield & Sacks

[57] ABSTRACT

A vitreous body prosthesis device comprises a thin-walled inflatable balloon made of silicone rubber. The balloon is provided with means for stabilizing and fixing the balloon within an eye to be treated. The balloon is provided with an inflow tube made of silicone rubber, the inflow tube being in fluid-tight communication with the interior of the balloon. The inflow tube leads to a bulb through which fluid can be introduced into, and removed from, the tube, whereby the degree of inflation of the balloon can be controlled, thereby gently forcing the thin-walled balloon against the retinal surface of the eye. A stabilizing tube may be provided, in which case it is in fluid communication with aqueous humor in the eye, and in fluid-tight communication with a silicone rubber drainage tube of an aqueous humor drainage device, which functions both as an anchoring object for the tubes and as a means of controlling eye pressure.

21 Claims, 2 Drawing Sheets

OTHER PUBLICATIONS

Cox, M. S., Trese, M. T., and Murphy, P. L., "Silicone Oil for Advanced Proliferative Vitreoretinopathy", Ophthalmology, 93:646-650, 1986.

Miyamoto, K., Refojo, M. F., Tolentino, F. I., Fournier, G. A., and Albert, D. M., "Fluorinated Oils as Experimental Vitreous Substitutes": Archives of Ophthalmology, 104:1053-1056, 1986.

Gabel, V. P., Kampik, A., Gabel, C. H., and Spiegel, D., "Silicone Oil with High Specific Gravity for Intraocular Use", British Journal of Ophthalmology, 71:262-267, 1987.

Refojo, M.; Leong, F.; Chung, H.; Ueno, N.; Nemiroff, B.; and Tolentino, F.; "Extraction of Retinol and Cholesterol by Intraocular Silicone Oils":, Ophtholmology, vol. 95, No. 5, pp. 614-618, May, 1988.

Freemen, H.; Schepens, C. and Couvillion, G.; "Current Management of Giant Retinal Breaks, Part II", *Tr. Am. Acad. Ophth. & Otol.*, 74:59-74, Jan.-Feb. 1970.

Couvillion, G.; Freeman, H.; and Schepens, C.; "Vitreous Surgery, III. Intra Ocular Balloon: Instrument Report", *Archives of Ophthalmology*, 83:713-714, Jun. 1970.

Freeman, H.; Couvillion, G.; and Schepens, C.; "Intraocular Balloon: Clinical Application", *Archives of Ophthalomology*, 83:715-721, Jun., 1970.

Tolentino, F.; Refojo, M.; Liu, H.; Schepens, C.; and Freeman, H.; "Intravitreous Silicone Balloon: An Experimental Study", *Ophthalmic Surgery*, vol. 9, No. 1, pp. 73-80, Feb. 1978.

VITREOUS BODY PROSTHESIS DEVICE

BACKGROUND OF THE INVENTION

This invention relates to a device which can be implanted within an eye in order to replace some of the functions formerly performed by a surgically-removed vitreous body, and possibly also the zonular ligaments and lens. Zonular ligaments hold the lens in a useful position on the visual axis of the eye, and the lens focusses light on the retina of the eye.

The vitreous body of an eye is made up of connective tissue substances, fibres and cells, and is the practically-transparent jelly-like object which occupies the posterior cavity in the eye. It has a surface layer next to the retina, which surface layer serves as a barrier to rapid passage of fluid into holes which may exist in the retina, thus preventing retinal detachment developing in locations where a retinal hole exists. The vitreous body thus effectively closes any holes which may develop in the retina. When the vitreous surface layer detaches from the retina, which occurs with age, after certain injuries, and in certain disease states, it is then more likely that any retinal holes which may be present, or which may develop later, will become associated with retinal detachment, a disease state which leads to loss of function of the photographic-film-like layer of nerve tissue lining the eyeball.

For retinal re-attachment surgery to be effective in the long term, retinal holes must be closed, so that fluid cannot pass through them, and new holes which tend to develop in certain eyes predisposed to develop retinal detachments must be closed by some means which prevents fluid flow through them.

One problem facing retinal surgeons is proliferative vitreoretinopathy, which requires surgical removal of the vitreous body before the retina may be re-attached. Existing methods of closing holes by scleral buckling in towards the inside of the eye, or internal tamponade with gas bubbles (whose effect lasts at most two weeks or so), or silicone oil injection (which can cause corneal edema and other complications) are not effective for the remainder of the patient's life in all cases.

In eyes which require internal tamponade with silicone oil, cataract not infrequently develops, and lenses are not infrequently removed from eyes with vitreous surgery, so some eyes lack both a lens and vitreous body.

The aim of the invention is to provide a vitreous body prosthesis device which can carry out the retinal hole closing functions of the vitreous body of an eye after this body has been removed during retinal re-attachment surgery.

SUMMARY OF THE INVENTION

The present invention provides a vitreous body prosthesis device comprising a thin-walled inflatable balloon made of bio-compatible material, means for stabilizing and fixing the balloon within an eye, an inflow tube made of bio-compatible material and in fluid-tight communication with the interior of the balloon, and means for introducing fluid into the inflow tube, or for removing fluid from the inflow tube, whereby the degree of inflation of the balloon can be controlled.

The balloon may have an inflated diameter of substantially 24 mm.

Advantageously, the balloon includes a thin elastic posterior portion for apposition to the retina of the eye, and a thicker, reinforced anterior portion. The thin elastic posterior portion of the balloon may have a thickness lying in the range of from 0.0001 mm to 2 mm, preferably substantially 0.06 mm; and the thicker, reinforced anterior portion of the balloon may have a thickness lying in the range of from 0.08 mm to 3 mm preferably substantially 0.5 mm. Preferably, said anterior portion supports an artificial concave, plano or convex lens, the lens being provided with indentations for facilitating lens manipulation by instruments. The lens may be made of polymethylmethacrylate or silicone rubber.

Protrusions on said anterior portion may constitute the means for stabilizing and fixing the device within the eye by ingrowing of connective tissues. Advantageously, said anterior portion is further reinforced by tube means, embedded fibres, or porous materials such as expanded open-celled silicone rubber foam or expanded polytetrafluoroethylene foam. The reinforcing tube means may be an endless (circular) tube passing round said anterior portion. Preferably, the anterior portion is provided with a plurality of short, open-ended tubes or open-celled silicone rubber foam, or expanded polytetrafluoroethylene foam, or attached biologically-inert woven or non-woven material, into which connective tissues can grow and form a means for attaching the device to the inner surface of the eye.

Advantageously, the balloon and the inflow tube are made of silicone rubber.

In a preferred embodiment, the means for introducing fluid into, and for removing fluid from, the inflow tube is constituted by a bulb at the end of the inflow tube and a hypodermic needle. Advantageously, the bulb is an extra-orbital, subcutaneous, thick-walled, silicone rubber injection bulb.

Preferably, the device further comprises a stabilizing tube which is fixed to said anterior portion of the balloon. In this case, the stabilizing tube may have an open end in fluid communication with aqueous humour in the eye and the stabilizing tube may lead to, and be in fluid-tight communication with, an aqueous humour drainage device, the stabilizing tube is joined to the drainage tube of the aqueous humour drainage device in a fluid-tight manner. Advantageously, the aqueous humour drainage device includes a drainage tube and a drainage body constituted by a silicone rubber band having a minimum width of 5 mm and a length sufficient to pass over, and be sutured to, the sclera of the eye in an equatorial position, the drainage tube being firmly fixed to the drainage body and opening directly onto a surface of the drainage body, wherein the aqueous humour drainage device is provided with a pressure gradient limiting valve having a predetermined opening pressure. Preferably, the stabilizing tube is joined to the drainage tube of the aqueous humour drainage device device in a fluid-tight manner. Conveniently, the stabilizing tube and the inflow tube are attached to the drainage body by sutures, clips or by weaving said tubes back and forth through perforations or slits in the drainage body.

BRIEF DESCRIPTION OF THE DRAWINGS

A vitreous body prosthesis device constructed in accordance with the invention will now be described, by way of example, with reference to the accompany drawings, in which.

DESCRIPTION OF PREFERRED EMBODIMENT

Figure 1:
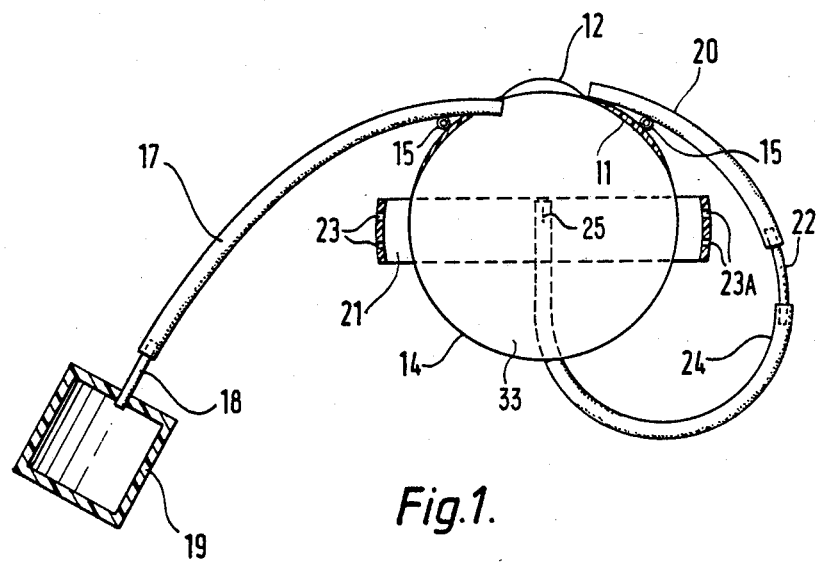
FIG. 1 is a part-sectional side elevation of the vitreous body prosthesis device together with a perforated aqueous humour drainage device.

Referring to the drawings, FIG. 1 shows a vitreous body prosthesis device having a delicate balloon 14 which is to function as an artificial vitreous surface layer to remain in contact with the retina of an eye. The balloon 14 has an anterior portion 11 and a posterior portion 33. The balloon 14 also includes a fluid inflow assembly comprising an inflow tube 17, a connecting tube 18 and a bulb 19. When inflated, the balloon 14 has a diameter of about 24 mm. The bulb 19 is a thick-walled silicone rubber bulb, into which a hypodermic needle can add or remove materials. The bulb 19 has an inner diameter of 5 mm and an outer diameter of 1 cm. The tube 18 connects the bulb 19 to the inflow tube 17 which is a medical grade silicone rubber inflow tube having an internal diameter of 0.3 mm and an outer diameter of 0.64 mm.

Figure 2:
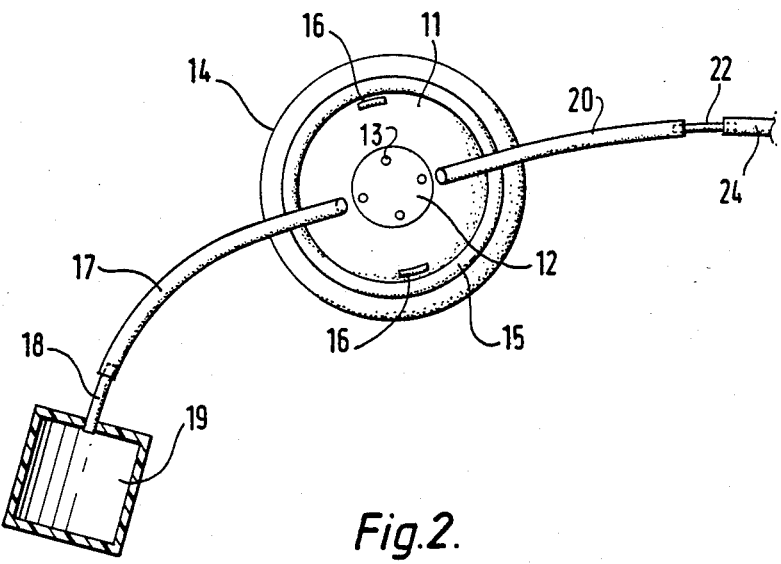
FIG. 2 is a front elevation of the vitreous body prosthesis device and an aqueous humour drainage device.
Figure 3A:
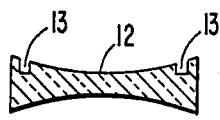
FIGS. 3A-3C are cross-sectional side views of concave lenses suitable for use with the present invention.
Figure 4A:
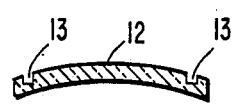
FIGS. 4A-4B are cross-sectional side views of plano lenses suitable for use with the present invention.
Figure 3B:
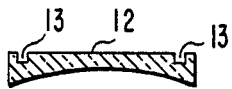
Figure 4B:
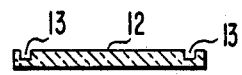
Figure 3C:
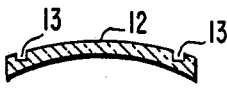
Figure 5A:
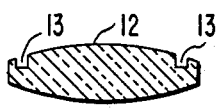
FIGS. 5A-5C are cross-sectional side views of convex lenses suitable for use with the present invention; and, FIG. 6 is a cross-sectional side view of a portion of the anterior portion of the balloon illustratively showing the disposition of embedded fibres within the material of the anterior portion and the location of attachments of perforated or porous material upon the anterior surface of the anterior portion of the balloon.
Figure 5B:
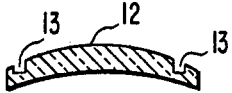
Figure 5C:
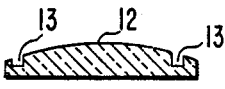

The inflow tube 17 passes through a reinforced anterior portion 11 of the balloon 14, and into the internal cavity of the balloon. The reinforced anterior portion 11 of the balloon 14 is constituted by a relatively-thick layer (0.5 mm) of silicone rubber, possibly with embedded polyester fibres 31, the remaining portion of the balloon having a thickness of about 0.06 mm. The thicker anterior portion 11 of the balloon 14 serves to prevent the balloon touching and damaging the cornea. The portion 11 is further reinforced by attached tubes 15 and 16. The tube 15 is an endless tube having an inner diameter of 0.3 mm and an outer diameter of 0.64 mm, and so has no open end into which fibrous tissue might grow. Thus, the tube 15 merely serves to increase the rigidity of the balloon wall. There are a large number of tubes 16 (only two of which are shown—see FIG. 2), each of which is a short length of open-ended tubing. The open ends of the tubes 16 serve to reinforce the balloon 14, and also enable intra-ocular fibrous tissue to grow into the open ends to attach the vitreous body prosthesis device to the ciliary body, in a similar manner to that in which the zonules are attached.

Figure 6:
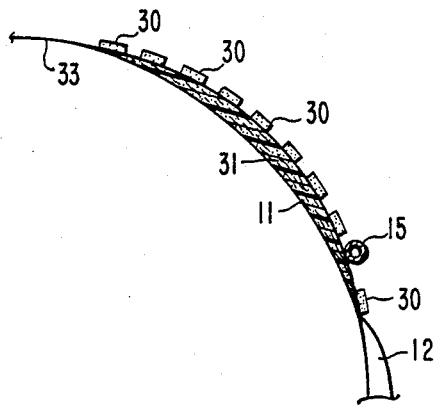

The tubes 16 may be made of expanded polytetrafluoroethylene. Instead of tubes 16, other perforated or porous attachments can be used. These attachments 30 (see, FIG. 6), such as polyester or other fibres woven, or otherwise formed, in a mesh, which would be infiltrated by fibroblasts, are attached to the reinforced anterior portion 11 of the balloon 14. An artificial intra-ocular lens 12 which may be concave, plano or convex, see, FIGS. 3A-3C, 4A-4B, and 5A-5C) is placed on the anterior surface of the device. The lens 12 includes a plurality of indentations 13 in its anterior surface which are useful in the manipulation and positioning of the lens. Also to position and stabilize the device, a second tube 20 is used, this tube also functioning as an exit from the eye for aqueous humour, which must be adequately drained to prevent glaucoma damage to the optic nerve. The tube 20 can be connected to, and be in fluid-tight communication with, a glaucoma drainage device which includes a drainage tube 24 and a drainage body constituted typically by a silicone rubber band 21 of width 9 mm. The drainage tube 24 drains aqueous humour from the anterior chamber of an eye, and the drainage band 21 distributes drained aqueous humour over a relatively large area. The drainage tube 24 is firmly fixed to, and opens directly onto the surface of, the drainage band 21. In use, the band 21 is sutured to the eye in a generally equatorial position. The drainage tube 24 is provided with a pressure gradient limiting valve 25.

In use, after the vitreous body and lens have been removed from the eye to be treated, the band 21 of the aqueous humour drainage device is placed at the equator of the eye and sutured to the sclera. Two cyclodialysis clefts are made 180° apart for the tubes 17 and 20, and a cataract incision is made. Sodium hyaluronate is introduced into the eye to protect the retina and the cornea from contact with the prosthesis device, and the tubes 20 and 17 are passed into the cataract incision and out of opposing cyclodialysis incisions and loosely attached to the drainage band 21 of the aqueous humour drainage device. Permissibly, the attachment of tubes 17 and 20 to the drainage band 21 may be accomplished by weaving those tubes respectively through perforations 23 and 23A in band 21. This creates a suitably firm frictional grip of the tubes 17 and 20 by the band 21 without occluding the lumen of either tube. The deflated balloon 14 is then gently inserted through the pupil, the balloon is slowly and gently inflated with physiologic salt solution, silicone oil or gas, and the optic nerve head observed for adequate circulation. The cataract incision is then closed. The tube 20 is connected to by a tube 22 the drainage tube 24 of the aqueous humour drainage device, and the tube 17 is connected to the extra-orbital bulb 19. The balloon inflation and implant positioning are continued, and the orbital and skin incisions closed.

Repeated adjustments to the volume of fluid in the vitreous body prosthesis device may be made by using the bulb 19 together with a syring and hypodermic needle.

If the delicate balloon 14 can be kept in adequately close contact with the retinal surface, retinal detachment is less likely to occur than if there were no silicone rubber membrane covering sites of old or new retinal holes.

It will be apparent that the vitreous body prosthesis device described above could be modified in a number of ways. For example, the prosthesis device can be used without the lens 12, the tube 20 or the aqueous humour drainage device. Moreover, the dimensions of the balloon 14, the tubes 17 and 15 and the bulbs 19 can be varied within wide limits. Thus, the thickness of the anterior portion 11 of the balloon 14 can lie within the range of from 0.08 mm to 3 mm, the thickness of the remaining portion of the balloon can lie within the range of from 0.0001 mm to 2 mm, the internal diameter of the tube 17 can lie within the range of from 0.15 mm to 0.6 mm, the outer diameter of the tube 17 can lie within the range of from 0.3 mm to 1.3 mm, the inner diameter of the tube 15 can lie within the range of from 0.15 mm to 2.5 mm, the outer diameter of the tube 15 can lie within the range of from 0.3 mm to 3 mm, the inner diameter of the bulb 19 can lie within the range of from 5 mm to 1 cm, and the outer diameter of the bulb 19 can lie within the range of from 1 cm to 3 cm, and the inflated diameter of the balloon can lie within the range of from 5 mm to 40 mm.

I claim:

1. A vitreous body prosthesis device for the replacement of a natural vitreous body comprising a thin-walled, inflatable and substantially spherical balloon having a posterior portion adapted for apposition to the retina of the eye and an anterior portion, said balloon being made of bio-compatible material; means for stabilizing and fixing the balloon within the vitreous cavity of the eye; an inflow tube made of bio-compatible material and in fluid-tight communication with the interior of the balloon; and, means for introducing fluid into the inflow tube, and for removing fluid from the inflow tube, whereby the degree of inflation of the balloon can be controlled.

2. A device according to claim 1, wherein the balloon has an inflated diameter of substantially 24 mm.

3. A device according to claim 1, wherein the posterior portion of the balloon is thinner than the anterior portion thereof.

4. A device according to claim 3, wherein the thin elastic posterior portion of the balloon has a thickness lying in the range of from 0.0001 mm to 2 mm.

5. A device according to claim 4, wherein the thin elastic posterior portion of the balloon has a thickness of substantially 0.06 mm.

6. A device according to claim 1, wherein the anterior portion of the balloon is thicker than said posterior portion, and includes reinforcement means.

7. A device according to claim 6, wherein the thicker, reinforced anterior portion of the balloon has a thickness lying in the range of from 0.08 mm to 3 mm.

8. A device according to claim 7, wherein the thicker, reinforced anterior portion of the balloon has a thickness of substantially 0.5 mm.

9. A device according to claim 6, wherein said anterior portion supports an artificial lens selected from the group consisting of concave lenses, plano lenses, and convex lenses.

10. A device according to claim 9, wherein the lens includes indentations for facilitating lens manipulation by instruments.

11. A device according to claim 9, wherein the material of the lens is selected from the group consisting of polymethylmethacrylate and silicone rubber.

12. A device according to claim 6, wherein protrusions on said anterior portion comprise the means for stabilising and fixing the device within the eye by ingrowing of connective tissues.

13. A device according to claim 6, wherein said reinforcement means is selected from the group consisting of tubular elements, embedded fibres, porous materials such as open-celled silicone rubber foam and expanded polytetrofluoroethylene foam, and biologically-inert woven and non-woven material.

14. A device according to claim 13, wherein the reinforcing tube means is an endless tube passing round said anterior portion.

15. A device according to claim 6, wherein the anterior portion includes means for fixing or attaching the device to the inner surface of the eye by the ingrowth of connective tissues, said means being selected from the group consisting of a plurality of short, open-ended tubes, open-celled silicone rubber foam, expanded polytetrafluoroethylene foam, and biologically-inert woven and non-woven material.

16. A device according to claim 1, wherein the balloon and the inflow tube are made of silicone rubber.

17. A device according to claim 1, wherein the means for introducing fluid into, and for removing fluid from, the inflow tube comprises a bulb at the end of the inflow tube and a hypodermic needle, and wherein the bulb is an extra-orbital, subcutaneous, thick-walled, silicone rubber injection bulb.

18. A device according to claim 6, further comprising a stabilizing tube which is fixed to said anterior portion of said balloon.

19. A device according to claim 18, wherein the stabilizing tube has an open end adapted to be in fluid communication with the aqueous humor in the eye, and the stabilizing tube leads to an aqueous humor drainage device.

20. A device according to claim 19, wherein the aqueous humour drainage device includes a drainage tube and a drainage body comprising a silicone rubber band having a minimum width of 5 mm and a length sufficient to pass over, and be sutured to, the sclera of the eye in an equatorial position, the drainage tube being firmly fixed to the drainage body and opening directly onto a surface of the drainage body, wherein the aqueous humour drainage device includes a pressure gradient limiting valve having a predetermined opening pressure.

21. A vitreous body prosthesis device for the replacement of a natural vitreous body comprising a thin-walled, inflatable balloon made of bio-compatible material having a posterior portion and an anterior portion, said posterior portion being thinner than said anterior portion and adapted for apposition to the retina of the eye and said anterior portion including reinforcing means; means for stabilizing and fixing said balloon in the vitreous chamber of the eye; an inflow tube made of bio-compatible material and in fluid-tight communication with the interior of said balloon; and, means for introducing fluid into the inflow tube and for removing fluid from the inflow tube, whereby the degree of inflation of the balloon can be controlled.

* * * * *